United States Patent
Zahn et al.

(10) Patent No.: US 8,148,548 B2
(45) Date of Patent: *Apr. 3, 2012

(54) HETEROCYCLIC FUSED SELENOPHENE MONOMERS

(75) Inventors: Steffen Zahn, Pennsburg, PA (US); Richard V. C. Carr, Allentown, PA (US); Roberta Kathleen Hause, Saylorsburg, PA (US); Carrie A. Costello, Troy, NY (US); Mark Mclaws, Ballston Lake, NY (US)

(73) Assignee: Konarka Technologies, Inc., Lowell, MA (US)

( * ) Notice: Subject to any disclaimer, the term of this patent is extended or adjusted under 35 U.S.C. 154(b) by 569 days.

This patent is subject to a terminal disclaimer.

(21) Appl. No.: 12/353,609

(22) Filed: Jan. 14, 2009

(65) Prior Publication Data

US 2009/0143599 A1    Jun. 4, 2009

Related U.S. Application Data

(63) Continuation-in-part of application No. 11/777,362, filed on Jul. 13, 2007.

(51) Int. Cl.
*C07D 495/04* (2006.01)
(52) U.S. Cl. .......................................................... 549/50
(58) Field of Classification Search ..................... 549/50
See application file for complete search history.

(56) References Cited

U.S. PATENT DOCUMENTS

| | | | |
|---|---|---|---|
| 3,574,217 A | 4/1971 | Wilhelm |
| 4,732,901 A | 3/1988 | Buckle |
| 5,300,575 A | 4/1994 | Jonas et al. |
| 6,585,914 B2 | 7/2003 | Marks et al. |
| 6,645,401 B2 | 11/2003 | Giles et al. |
| 6,676,857 B2 | 1/2004 | Heeney et al. |
| 6,695,978 B2 | 2/2004 | Worrall et al. |
| 6,709,808 B2 | 3/2004 | Lelental et al. |
| 7,071,289 B2 | 7/2006 | Sotzing |
| 7,125,479 B2 | 10/2006 | Sotzing |
| 7,700,008 B2 | 4/2010 | Hsu et al. |
| 7,722,785 B2 | 5/2010 | Hsu et al. |
| 2004/0010115 A1 | 1/2004 | Sotzing |
| 2006/0074250 A1 | 4/2006 | Zahn et al. |
| 2006/0076557 A1 | 4/2006 | Waller |
| 2007/0170401 A1 | 7/2007 | Hsu et al. |
| 2007/0278453 A1 | 12/2007 | Zahn et al. |
| 2007/0278458 A1 | 12/2007 | Martello et al. |
| 2008/0023676 A1 | 1/2008 | Hsu |
| 2009/0140219 A1 | 6/2009 | Zahn |
| 2009/0278093 A1 | 11/2009 | Heeney et al. |

FOREIGN PATENT DOCUMENTS

| | | |
|---|---|---|
| EP | 0 194 093 | 9/1986 |
| EP | 1 318 163 | 6/2003 |
| EP | 1 559 739 | 8/2005 |
| EP | 1 642 896 | 4/2006 |
| EP | 1 652 850 A1 | 5/2006 |
| EP | 1 728 810 A1 | 12/2006 |
| EP | 1 754 736 | 2/2007 |
| EP | 2 014 664 A2 | 1/2009 |
| EP | 2 014 665 A2 | 1/2009 |
| JP | 2005-035955 A | 2/2005 |
| KR | 2003/0047749 | 6/2003 |

OTHER PUBLICATIONS

Yasuike, Syntheses of Novel Group I5 and I6 Thieno[2,3-b]-,thieno[3,4-b]-, and thieno[3,2-b]-heteroles, 1997, Heterocycles, vol. 45, No. 10, p. 1891-1894.*
Abronin et al., "Quantum chemical analysis of selenium-77 chemical shifts in condensed selenophenes", Chem. Scripta (1982), 29(3), 75-7 (Abstract Only).
Beletskaya, et al., "The Heck Reaction As a Sharpening Stone of Palladium Catalysis," Chem. Rev. 2000, 100, pp. 3009-3066.
Fagnou, et al. "Rhodium-Catalyzed Carbon-Carbon Bond Forming Reactions of Organometallic Compounds", Chem. Rev. 2003, 103, pp. 169-196.
Guliev et al., "Quantum-chemical calculations of spectroscopic parameters of heteroaromatic sulfur and selenium compounds", Izvestiya Akademi Nauk SSSR, Seriya Khimicheskaya (1986), (10, 2251-3 (Abstract Only).
H Atom Adducts-New Free Radicals? J. Am. Chem. Soc. 85, 484 (1963).
Hassan et al., "Aryl-Aryl Bond Formation One Century After the Discovery of the Ullman Reaction", Chem. Rev. 2002, 102, pp. 1359-1469.
Jones, et al., "The Vilsmeir reaction of fully conjugated carbocycles and heterocycles", Organic Reactions (Hoboken, NJ) (1997), 49, no pages given (Abstract Only).
Miyaura et al., "Palladium-Catalyzed Cross-Coupling Reactions of Organoboron Compounds", Chem. Rev. 1995, 95, pp. 2457-2483.
Negishi, et al., Palladium-Catalyzed Alkynylation, Chem. Rev. 2003, 103. p. 1979-2017.
Novak "Structure, stability and aromaticity of bis-heteropentalenes", Theochem (1997, 398-399, 315-323 (Abstract Only).
Walker, et al., "New Chemically Conducting Pyrrole Blacks", J. Polym. Sci. Part A Polym. Chem., vol. 26, pp. 1285-1294 (1988).
Yasuike, S., et al; "Syntheses of Novel Group 15 and 16 Thieno[2,3-b]-, Thieno[3,4-b]-, and Thieno [3,2-b]-Heteroles"; vol. 45, No. 10; 1997; pp. 1891-1894; XP-001537354.
Litvinov, V.P., et al; "Selenopheno[2,3-c] Thiopene—A Third Isomeric Selenophenothiophene"; vol. 20, No. 7; 1971; p. 1498; XP-002580629.

(Continued)

*Primary Examiner* — Noble Jarrell
*Assistant Examiner* — Karen Cheng
(74) *Attorney, Agent, or Firm* — Fish & Richardson P.C.

(57) ABSTRACT

A heterocyclic fused selenophenes and a method of making a heterocyclic fused selenophenes of formula (1):

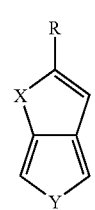

(1)

wherein X is S or Se, Y is S or Se, wherein one or both of X and Y is Se, R is a substituent group. The monomer being capable of polymerization to form an electrically conductive polymer or oligomer.

13 Claims, No Drawings

OTHER PUBLICATIONS

Kulik, W., et al; "Dimetalation of Isopropenylacetylene. Application in the Synthesis of 3-Methylselenophen, 3-Methylene-2,3-Dihydroselenophen and the Tellurium Analogues"; vol. 24, No. 21; 1983; pp. 2203-2204; XP-002580630.

Konar, A, et al; "Selenolo [3,4-b] Selenophene—The Third 'Classical' Selenophene;" Tetrahydron, vol. 36, (1980) ;; 3317-3323.

Yasuike, Shuji; et al; "Syntheses of Novel Group 15 and 16 Thieono[2,-3-b], Thieno[e,4-b]-, and Thieno[3,2-b]-Heteroles;" Heterocycles, vol. 48, No. 10, 1997; pp. 1891-1894.

Shuji Yasuike, et al; "Syntheses of Novel Group 15 and 16 Thieno[2,3-b]-, Thieno[3,4-b]-, and Thieno[3.2-b] Heteroles"; Heterocycles; vol. 45, No. 10; 1997; pp. 1891-1894; XP1537354.

Litvinov, V.P., et al; "Selenopheno[2,3-c]Thiophene—A Third Isomeric Selenophenothiophene"; Russian Chemcial Bulletin; vol. 20, No. 7; 1971; p. 1498; XP002580629.

Kulik, W., et al; "Dimetalation of Isopropenylacetylene Application in the Synthesis of 3-Methylselenophen, 3-Methylene-2,3-Dihydroselenophen and the Tellurium Analogues"; Tetrahedron Letters; vol. 24, No. 21; 1983; pp. 2203-2204; XP002580630.

John, J.A., et al; "Synthesis of Polyphenylene Derivatives by Thermolysis of Enediynes and Dialkynylaromateic Monomers"; Tetrahedron, Elsevier Science Publishers; vol. 53, No. 45; Nov. 10, 1997; pp. 15515-15534; XP004106381.

Shuji Yasuike, et al; "Synthesis of Novel Dithieno[2,3-b,3', 2'-f]- and Dithieno[3,4-b;3', 4'-f]Heteroepins Containing Group 14, 15 and 16 Heavier Elements"; Heterocycles; vol. 45, No. 10; Oct. 1, 1997; pp. 1899-1902; XP001539729.

Gronowitz, S.; "New Syntheses of 3-Bromo-Thiophene and 3,4-Dibromo-Thiophene"; Acta Chem. Scand.; vol. 13, No. 5; 1959; pp. 1045-1046; XP002594517.

Ye, X-S., et al; "Synthetic Applications of 3,4-Bis9Trimethylsilyl)Thiophene: Unsymmetrically 3,4-Disubstituted Thiophenese and 3,4-Didehydrothiophene"; J. Org. Chem.; vol. 62; 1997; pp. 1940-1954; XP002594518.

Claude Paulmier, et al., "N° 434.—Syntheses des derives di et triformyles du thiophene et du selenophene", Bulletin de la Societe Chimique de France, 1969, pp. 2511-2518.

Gronowitz, Salo, et al., Proton, carbon-13, and selenium-77 NMR spectra of compounds of the selenopheno[2,3-c]thiophene series, Izvestiya Akademii Nauk SSSR, Seriya Khimicheskaya, No. 6, 1981, pp. 1285-1289.

Konar, Andreas, et al., "Selenolo [3,4-b] thiophene—the Fourth "Classical" Selenolothiophene", Chemica Scripta, vol. 19, 1982, pp. 176-181.

Konar, Andreas, et al., "On the Electrophukuc Substitution and Metalation of Selenoloselenophenes", Chemica Scripta, vol. 22, 1983, pp. 177-181.

Nakayama J., et al., "A Novel Synthesis of Selenophenes", Tetrahedron Letters, vol. 29, No. 12, 1988, pp. 1399-1400.

Neef, C.J., et al., "Synthesis and Electronic Properties of Poly(2-phenylthieno[3,4-b]thiophene): A New Low Band Gap Polymer", Chem. Mater., vol. 11, 1999, pp. 1957-1958.

Ng, S. C., et al., "Synthesis and Characterization of Poly{1,2.bis(2-seleninyl)ethene}, a Novel Electrically Conductive Polymer with Diminished Band Gap", Macromolecules, vol. 31, No. 4, 1998, pp. 1221-1228.

Pomerantz, et al., "Poly(2-decylthieno[3,4-b]thiophene). A New Soluble Low-Bandgap Conducting Polymer", Synthetic Metals, vol. 84, No. 1-3, 1997, pp. 243-244.

Ruban, G. et al., "Synthese, Charakterisierung und Kristallstruktur von Bis{4-(2-thienyl)selenolo[3,4-b] thiophen-6-yl}diselenid", Chem. Ber., vol. 114, 1981, pp. 818-821.

Yasuike et al., "Syntheses of Novel Group 15 and 16 Thieno[2,3-b]-, Thieno[3,4-b]-, and Thieno[3,2-b]-Heteroles", Heterocycles, vol. 45, No. 10, Oct. 1, 1997, pp. 1891-1894.

Yoshio Aso, et al., "3,4-Thienylene-ethynylene Oligomers" Phosphorus, Sulfur and Silicon and the Related Elements, vol. 120 & 121, 1997, pp. 417-418.

Konar. A, et al; "Selenolo[3,4-b]Selenophene—The Third "Classical" Selenophtene"; Tetrahedron; vol. 36, No. 22; pp. 3317-3323; 1980.

Yavuz, M.S., et al; "Optically Transparent Conducting Polymers from Fused Heterocycles"; Material Research Society Proceeding; vol. 965, 2007.

Ketcham, R.; "Synthesis of Tetrathiafulvalene Doubly Fused to the 3,4-Position of Selenophene"; J. Org. Chem.; vol. 49; pp. 1117-1119; 1984.

* cited by examiner

HETEROCYCLIC FUSED SELENOPHENE MONOMERS

CROSS-REFERENCE TO RELATED APPLICATIONS

This Application is a continuation in part of U.S. patent application Ser. No. 11/777,362, filed on Jul. 13, 2007; the disclosure of which is hereby incorporated by reference.

The subject matter of this application is related to U.S. patent application Ser. No. 11/777,386, filed on Jul. 13, 2007, and application Ser. No. 12/353,461, filed on even date herewith, and entitled "SELENIUM CONTAINING ELECTRICALLY CONDUCTIVE POLYMERS AND METHOD OF MAKING ELECTRICALLY CONDUCTIVE POLYMERS"; the disclosure of which is hereby incorporated by reference.

BACKGROUND OF THE INVENTION

The present disclosure is directed to monomers and methods for making monomers for forming electrically conductive polymers.

Electrically conducting polymers have found use in a variety of organic optoelectronics applications. Such optoelectronic applications include polymeric light emitting diodes (thin film displays), solid-state lighting, organic photovoltaics, advanced memory devices, organic field effect transistors, ultracapacitors, electroluminescent devices, printed electronics, conductors, lasers, and sensors.

One of the first electrically conducting polymers was polyacetylene and the discovery of conductivity in such polymer created substantial interest in other types of electrically conducting polymers. Recently, conjugated poly(thiophenes) and substituted thiophene derivatives have been discovered to have electrically conducting properties. A feature of these polymers is that they can be cast into films and doped with conventional p- and n-type dopants. Additionally, the doped polymers can be cast into films and their electrical properties modified accordingly, thereby lending themselves suitable for use in a variety of optoelectronic applications.

Known thiophene monomers and electrically conducting polymers including thiophene and derivatives thereof include the following:

U.S. Patent Application Publication No. U.S. 2004/00010115A1 to Sotzing discloses homopolymers and copolymers comprised of repeating units of thieno[3,4-b]thiophene for use in electroactive applications. The thieno[3,4-b]thiophene compounds disclosed in the US2004/00010115A1 include the following structure:

U.S. Patent Application Publication No. U.S. 2004/00010115A1 further discloses that copolymers can be formed with compounds including 3,4-ethylendioxythiophene, dithiophene, pyrrole, and benzothiophene.

U.S. Pat. No. 6,645,401 to Giles et al. discloses conjugated polymers of dithienothiophene (DTT) with vinylene or acetylene connecting groups as suitable for producing semiconductors or charge transport materials useful in electrooptical and electronic devices including field effect transistors ("FET"), photovoltaic, and sensor devices.

U.S. Pat. No. 6,585,914 to Marks discloses fluorocarbon-functionalized and/or heterocyclic modified poly (thiophenes) such as α, ω-diperfluorohexylsexithiophene for use in forming films, which behave as n-type semiconductors. These poly(thiophenes) also can be used to form thin film transistors with FET mobility.

U.S. Pat. No. 6,676,857 to Heeney et al. discloses polymers having polymerized units of 3-substituted-4-fluorothiophene as liquid crystal materials for use in semiconductors, charge transport materials, electrooptical field effect transistors, photovoltaic and sensor devices.

U.S. Pat. No. 6,695,978 to Worrall et al. discloses polymers of benzo[b]thiophene and bisbenzo[b]-thiophene and their use as semiconductors and as charge transport materials in electrooptical devices.

U.S. Pat. No. 6,709,808 to Lelental et al. discloses image-forming materials incorporating electrically conductive polymers based upon pyrrole-containing thiophene polymers and aniline containing polymers.

Tetrahedron 1940, 36, 3317-3324 by Gronowitz discloses the preparation of seleno(3,4-b)selenophene. The synthesis utilizes a decarboxylation procedure that is commonly seen as being problematic if exploited at a commercial scale.

Heterocycles 1997, 45, 1891-1894 discloses the preparation of selenolo(2,3-c)thiophene by a multistep route. Multistep routes have been shown to be useful for synthesizing materials at small scale, but are generally not favored for large scale, industrial setups.

While the above references include disclosures of known monomer compounds and methods of making these known monomer compounds, none of the above references discloses substituted seleno(3,4-b)selenophenes, seleno(2,3-c)thiophenes, or thiophene(3,4-b)selenophenes monomers or methods of making fused selenophene monomers of the present disclosure.

The disclosure of the foregoing patents, patent applications and publications is hereby incorporated by reference in their entirety.

What is needed is a monomer capable of forming an electrically conductive polymer for a wide range of electronic applications. There is also a need in this art for a monomer that can be formed using readily available, easily handled reagents and which can be polymerized.

BRIEF SUMMARY OF THE INVENTION

One aspect of the present disclosure includes a method of making a compound of formula (1):

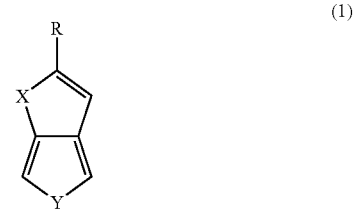

(1)

wherein X is S or Se, Y is S or Se, wherein one or both of X and Y is Se, R is a substituent group. R may be any substituent group capable of bonding to the ring structure. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that 0 and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F. R' and R" are independently of each other H, aryl or alkyl with 1 to 12 C— atoms. The method includes providing a first reactant having the formula (2):

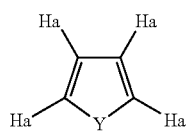

(2)

wherein Y is defined above and Ha is a halogen-containing group. The first reactant is reduced in the presence of a metal reducing agent to form a second reactant having the formula (3):

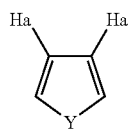

(3)

wherein Y and Ha are defined above. The second reactant is then reacted with a substituted 1-alkyne in the presence of a transition metal catalyst in order to form a third reactant, the third reactant having the formula (4):

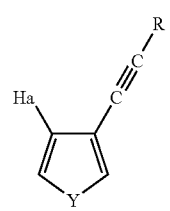

(4)

wherein R, Y and Ha are defined above. The third reactant is then reacted with an alkyl lithium in the presence of a compound comprising X, X being defined above, to produce a fourth reactant having the formula (5):

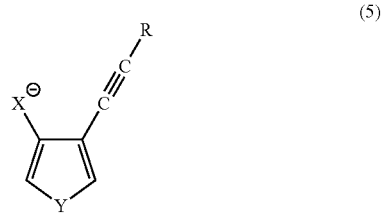

(5)

wherein R, X, and Y are defined above. The fourth reactant is then reacted with water to form the compound having formula (1).

Another aspect of the present disclosure includes a method for making heterocyclic fused selenophenes according to the following formula (4):

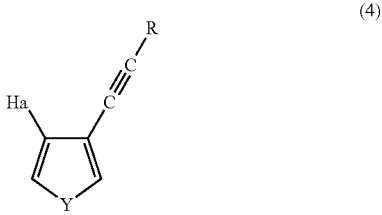

(4)

wherein X is S or Se, Y is S or Se, wherein one or both of X and Y is Se, R is a substituent group and may include the moieties discussed above with respect to formula (1). The method further includes providing a first reactant having the formula (2):

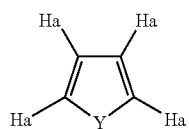

(2)

wherein X is defined above and Ha is a halogen-containing group. The first reactant is reduced in the presence of a metal reducing agent to form a second reactant having the formula (3):

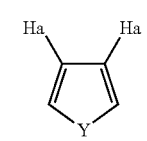

(3)

wherein Y and Ha are defined above. The second reactant is then reacted with a substituted 1-alkyne in the presence of a transition metal catalyst in order to form the compound according to formula (4):

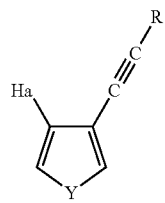

(4)

wherein Y, Ha and R are defined above.

Another aspect of the present disclosure includes a method of making a compound of formula (1):

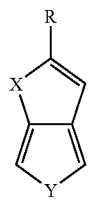

(1)

wherein X is S or Se, Y is S or Se, wherein one or both of X and Y is Se, R is a substituent group and may include the moieties discussed above with respect to formula (1). The method further includes providing a having the formula (4):

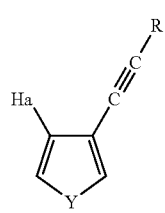

(4)

wherein R and Y are defined above and Ha is a halogen-containing group. The reactant is then reacted with an alkyl lithium in the presence of a compound comprising X, X being defined above, to produce a reactant having the formula (5):

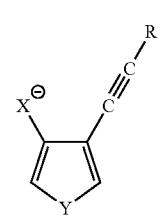

(5)

wherein R, X, and Y are defined above. The fourth reactant is then reacted with water to form the compound having formula (1).

Another aspect of the present disclosure includes a method of making a compound of formula (6):

(6)

wherein X is S or Se, Y is S or Se, wherein one or both of X and Y is Se. The method further includes providing a reactant according to formula (7):

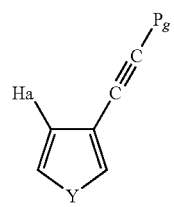

(7)

wherein Y is defined above and Ha is a halogen-containing group. $P_g$ is a hydrolysable protecting group. The reactant is then reacted with an alkyl lithium in the presence of a compound comprising X, X being defined above, to produce a reactant according to formula (8):

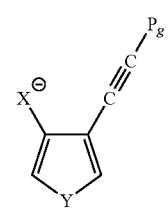

(8)

wherein $P_g$, X, and Y are defined above. The reactant is then reacted with water to form the compound having formula (6).

Another embodiment of the present disclosure includes heterocyclic monomer compounds according to the following formula:

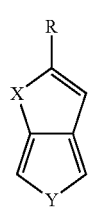

wherein X is S or Se, Y is S or Se, wherein one or both of X and Y is Se, R is a substituent group. R may include hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments, R may include alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R''—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F, R' and R'' are independently of each other H, aryl or alkyl with 1 to 12 C-atoms.

Another embodiment of the present disclosure includes heterocyclic fused compounds imidazolone, dioxolone, imidazolethione or dioxolethione including 2-phenyl-selenolo[2,3-c]thiophene (1a), 2-phenyl-selenolo[3,4-b]thiophene (1b) and 2-phenyl-selenolo[3,4-b]selenophene (1c), and the thiocarbonyl compounds 2-hexyl-selenolo[2,3-c]thiophene (1d), 2-hexyl-selenolo[3,4-b]thiophene (1e) and 2-hexyl-selenolo[3,4-b]selenophene (1f), all shown by the following structures:

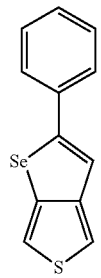

1a

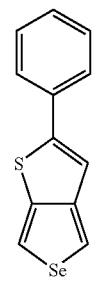

1b

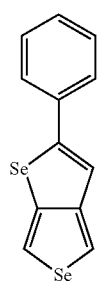

1c

-continued

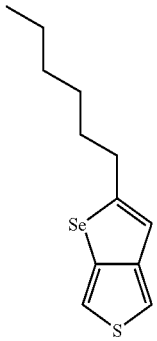

1d

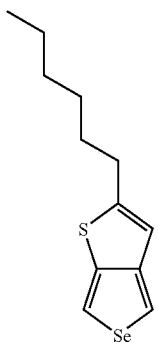

1e

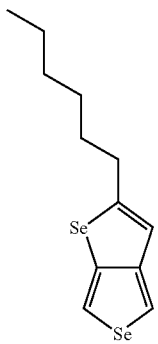

1f

Another embodiment of the present disclosure includes a heterocyclic monomer compound according to the following formula:

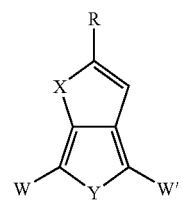

wherein X is S or Se, Y is S or Se, wherein one or both of X and Y is Se, R is a substituent group and may include the moieties discussed above with respect to formula (1)

Another embodiment of the present disclosure includes a compound having the following formula:

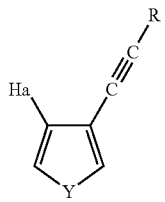

wherein Y is S or Se, R is a substituent group and may include the moieties discussed above with respect to formula (1) and Ha is a halogen-containing group.

Another embodiment of the present disclosure includes a compound having the following formula:

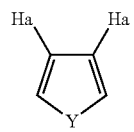

wherein Y is Se, Ha is a halogen containing group.

The disclosure includes heterocyclic fused selenophene based monomers. Such monomers and polymers derived therefrom, find use in applications, including, but not limited to, hole injection materials, charge transport materials, semiconductors, and/or conductors, in optical, electrooptical or electronic devices, polymeric light emitting diodes (i.e., PLED), electroluminescent devices, organic field effect transistors (i.e., FET or OFET), flat panel display applications (e.g., LCD's), radio frequency identification (i.e., RFID) tags, printed electronics, ultracapacitors, organic photovoltaics (i.e., OPV), sensors, lasers, small molecule or polymer based memory devices, electrolytic capacitors, anti-corrosion coatings, or as hydrogen storage materials.

One advantage of a method according to an embodiment of the present disclosure includes preparation of previously unknown substituted selenophene monomers having an extended range of performance in many electronic applications.

Another advantage of a method according to an embodiment of the present disclosure includes preparation of heterocyclic fused selenophene monomers. In one aspect the inventive methods can be conducted without the necessity of using decarboxylation chemistries.

Still another advantage of a method according to an embodiment of the present disclosure includes preparation of heterocyclic selenophene monomers in high yield, providing for an efficient, cost effective process. For example, the inventive process can produce a monomeric product having at least about 65 mol % monomer.

An advantage of an embodiment of the present disclosure is that heterocyclic fused selenophene monomers and derivatives thereof may be used to produce conductive polymers having low work functions (e.g., polymers a conductivity of at least about $10^{-5}$ S/cm). For example, the present disclosure includes monomers for fabricating polymers suitable as a hole injecting material.

Another advantage of an embodiment of the present disclosure is that heterocyclic fused selenophene monomers and derivatives thereof may be used to produce conducting polymers having a low band gap (e.g., a band gap of about <2.5 eV). For example, the present disclosure includes monomers for fabricating polymers suitable as transparent conductors.

Still another advantage of an embodiment of the present disclosure is that heterocyclic fused selenophene monomers and derivatives thereof may be used to produce conducting polymers having a wide range of electronic applications.

Still another advantage of an embodiment of the present disclosure is that heterocyclic fused selenophene monomers and derivatives thereof may be used to produce a hole injection material having desirable properties including a substantially identical work function level between the hole injection layer ("HIL") material and the light emitting layer in an electroluminescent device.

Still another advantage of an embodiment of the present disclosure is that heterocyclic fused selenophene monomers and derivatives thereof may be used to produce an oxidized form of the polymer. The resultant polymer can possess desirable properties including the formation of a highly delocalized ionic polymer having high conductivity.

Still another advantage of an embodiment of the present disclosure is that heterocyclic fused selenophene monomers and derivatives thereof may be used to produce solution processible materials.

Still another advantage of an embodiment of the present disclosure is that monomers based upon heterocyclic fused selenophenes and derivatives thereof may be used to produce an environmentally stable semiconducting polymer.

Other features and advantages of the present disclosure will be apparent from the following more detailed description of certain embodiments, taken in conjunction with the accompanying drawings which illustrate, by way of example, the principles of the disclosure.

DETAILED DESCRIPTION OF THE INVENTION

"Fused" is defined as sharing a common bond within the ring between a thiophene and a selenophene or a selenophene and a selenophene, thereby connecting the ring structures together.

The disclosure includes a method for making heterocyclic fused selenophenes according to the following formula (1):

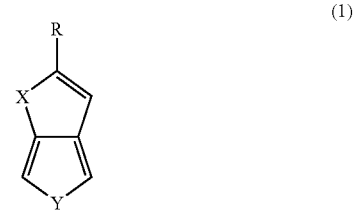

wherein X is S or Se, Y is S or Se, wherein one or both of X and Y is Se, R is a substituent group. R may be any substituent group capable of bonding to the ring structure. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, aryisulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F, R' and R" are independently of each other H, aryl or alkyl with 1 to 12 C-atoms. The method further includes providing a first reactant having the formula (2):

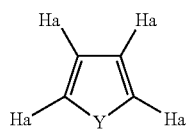

(2)

wherein Y is defined above and Ha is a halogen containing group. The halogen containing group may include, but is not limited to, Cl, Br or I. The first reactant is reduced in the presence of a metal reducing agent to form a second reactant having the formula (3):

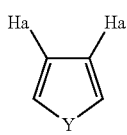

(3)

wherein Y and Ha are defined above. The metal reducing agent may include any metal reducing agent suitable for reducing the first reactant and may include, but is not limited to zinc or magnesium. The second reactant is then reacted with a substituted 1-alkyne in the presence of a transition metal catalyst in order to form a third reactant, the third reactant having the formula (4):

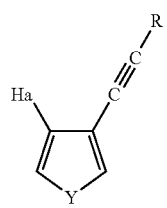

(4)

wherein R, Y and Ha are defined above. The transition metal catalyst may include, but is not limited to, platinum group containing catalysts, such as palladium dichloride-bis-triphenylphosphine or other systems that may be used in Sonogashira coupling chemistry. The substituted 1-alkyne includes functional groups having the following formula:

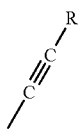

R may be any substituent group capable of bonding to the triple bonded carbon. R may include alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments, R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F, R' and R" are independently of each other H, aryl or alkyl with 1 to 12 C-atoms. The third reactant is then reacted with an alkyl lithium in the presence of a compound comprising X, X being defined above, to produce a fourth reactant having the formula (5):

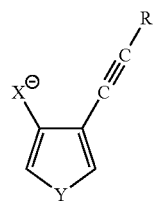

(5)

wherein R, X, and Y are defined above. The alkyl lithium may include alkyl containing lithium compounds, such as, but not limited to n-butyl, secondary and tertiary-butyl lithium or other alkyl lithium agents. The compound comprising X may include compounds that contain sulfur, selenium or combinations thereof. Suitable compounds include, but are not limited to selenium powder and sulfur ($S_8$). The fourth reactant is then reacted with water to form the compound having formula (1).

This disclosure provides a method for making heterocyclic fused selenophenes according to the following formula (4):

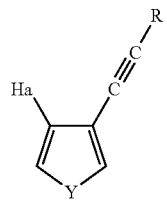
(4)

wherein X is S or Se, Y is S or Se, wherein one or both of X and Y is Se, R is a substituent group and may include the moieties discussed above with respect to formula (1). The third reactant is then reacted with an alkyl lithium in the presence of a compound comprising X, X being defined above, to produce a fourth reactant having the formula (5):

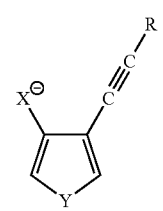
(5)

wherein R, X, and Y are defined above. The fourth reactant is then reacted with water to form the compound having formula (1).

The present disclosure further includes a method of making a compound of formula (1):

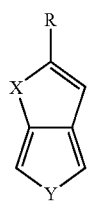
(1)

wherein X is S or Se, Y is S or Se, wherein one or both of X and Y is Se, R is a substituent group and may include the moieties discussed above with respect to formula (1). The method further includes providing a having the formula (4):

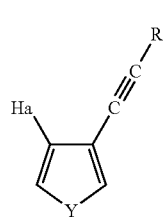
(4)

wherein R, Y and Ha are defined above. The reactant is then reacted with an alkyl lithium in the presence of a compound comprising X, X being defined above, to produce a reactant having the formula (5):

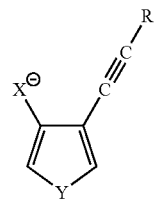
(5)

wherein R, X, and Y are defined above. The fourth reactant is then reacted with water to form the compound having formula (1).

The present disclosure further includes a method of making a compound of formula (1):

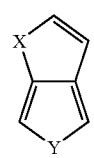
(6)

wherein X is S or Se, Y is S or Se, wherein one or both of X and Y is Se. The method further includes providing a compound having the formula (7):

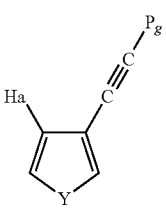
(7)

wherein Y and Ha are defined above. $P_g$ is a hydrolysable protecting group. The hydrolysable protecting group may be any suitable protecting group that is capable of hydrolyzing and may include, but is not limited to trimethyl silyl or tert-butyldimethyl silyl. The reactant is then reacted with an alkyl lithium in the presence of a compound comprising X, X being defined above, to produce a reactant having the formula (8):

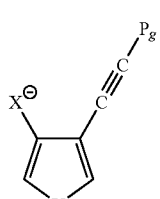
(8)

wherein $P_g$, X, Y and Ha are defined above. The reactant is then reacted with water to form the compound having formula (6).

This disclosure further includes heterocyclic fused selenophene monomeric compounds according to the following formula (1):

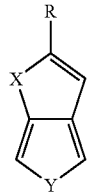

(1)

wherein X is S or Se, Y is S or Se, wherein one or both of X and Y is Se, R is a substituent group. R may be any substituent group capable of bonding to the ring structure. R may include hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F, R' and R" are independently of each other H, aryl or alkyl with 1 to 12 C-atoms Another embodiment of the present disclosure includes heterocyclic fused selenophene compounds including 2-phenyl-selenolo[2,3-c]thiophene (1a), 2-phenyl-selenolo[3,4-b]thiophene (1b) and 2-phenyl-selenolo[3,4-b]selenophene (1c), and the thiocarbonyl compounds 2-hexyl-selenolo[2,3-c]thiophene (1d), 2-hexyl-selenolo[3,4-b]thiophene (1e) and 2-hexyl-selenolo[3,4-b]selenophene (1f), all shown by the following structures:

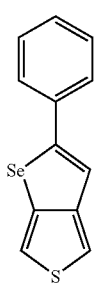

1a

-continued

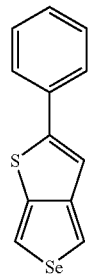

1b

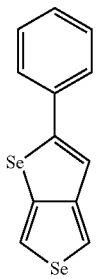

1c

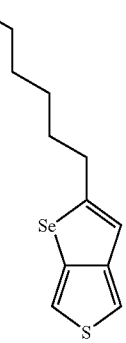

1d

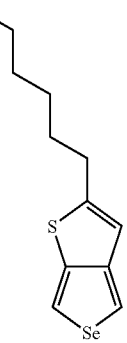

1e

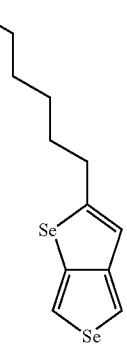

1f

In another embodiment of the present disclosure, derivatives of the heterocyclic fused selenophenes formed prior to or after the formation of the fully aromatic fused heterocyclic monomer.

Another embodiment of the present disclosure includes a compound having the following formula:

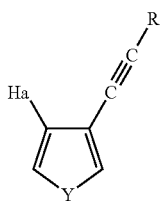

wherein Y is S or Se, R is a substituent group and may include the moieties discussed above with respect to formula (1) and Ha is a halogen containing group.

Another embodiment of the present disclosure includes a compound having the following formula:

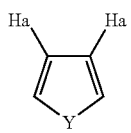

wherein Y is Se, Ha is a halogen containing group. In certain embodiments Ha is independently Br or I and combinations of Br and I on the same molecule.

Monomer derivatives according to the present disclosure may include compounds having the following formula:

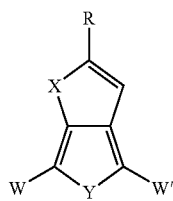

wherein X is S or Se, Y is S or Se, wherein one or both of X and Y is Se, R is a substituent group. R may be any substituent group capable of bonding to the ring structure of P1. R may include hydrogen or isotopes thereof, hydroxyl, alkyl, including $C_1$ to $C_{20}$ primary, secondary or tertiary alkyl groups, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, or alkyl or phenyl substituted with one or more sulfonic acid (or derivatives thereof), phosphoric acid (or derivatives thereof), carboxylic acid (or derivatives thereof), halo, amino, nitro, hydroxyl, cyano or epoxy moieties. In certain embodiments R may include alpha reactive sites, wherein branched oligomeric, polymeric or copolymeric structures of the selenium containing ring structure may be formed. In certain embodiments, R may include R may include hydrogen, alkylaryl, arylalkyl, aryl, heteroaryl, $C_1$ to $C_{12}$ primary, secondary or tertiary alkyl groups, which may be mono- or polysubstituted by F, Cl, Br, I or CN, and wherein one or more non-adjacent CH2 groups may be replaced, independently with —O—, —S—, —NH—, —NR'—, —SiR'R"—CO—, —COO—, —OCO—, —OCO—O—, —S—CO—, —CO—S—, —CH═CH— or —C≡C— in such a manner that O and/or S atoms are not linked directly to one another, phenyl and substituted phenyl groups, cyclohexyl, naphthalenic, hydroxyl, alkyl ether, perfluoroalkyl, perfluoroaryl, carboxylic acids, esters and sulfonic acid groups, perfluoro, $SF_5$, or F, R' and R" are independently of each other H, aryl or alkyl with 1 to 12 C-atoms. W and W' are H, halogen atoms, e.g., F, Cl, Br, and I, metallorganics, e.g., MgCl, MgBr, MgI, $Sn(R_2)_3$, where $R_2$ is $C_{1-6}$ alkyl or $C_{1-6}$ alkyl ether, boronic acid, boronic ester, vinyl units, e.g., —CH═CHR₃ where R₃ is H or $C_{1-6}$ alkyl, ether, i.e., —$OC_{1-6}$ alkyl, esters, i.e., —COO$C_{1-6}$ alkyl, —S—COR₄ and —COR₄ where R₄ is H or $C_{1-6}$ alkyl, —C≡CH, and polymerizable aromatic rings such as phenyl, naphthalene, pyrrole, and thiophene. Derivatives of the substituted claimed compositions can be formed prior to or after addition of the secondary or tertiary functionality.

The polymerization and the resulting polymer can be controlled by selecting moieties W and W' having the desired polymerization reaction and desired resultant polymer. Carbon-carbon bond forming reactions may be completed following any suitable method. Methods suitable for use with the monomer of the present disclosure include, but are not limited to the Suzuki Reactions, the Yamamoto Reactions, the Heck Reactions, the Stille Reactions, the Sonogashira-Hagihara Reactions, the Kumada-Corriu Reactions, the Riecke Reactions, and the McCullogh Reactions.

Derivatives according to the present disclosure may include homopolymers and copolymers in which W and W' are H. In another embodiment, the compounds of the present disclosure may include homopolymer and copolymers wherein W, and W' are Br. In still another embodiment, the compounds of the present disclosure may include homopolymer and copolymers wherein W, and W' are trialkylstannyl.

Many of the derivatives of the respective monomers where W and W' are other than H are formed post-formation of the monomers. In one such post-reaction, one or both hydrogen atoms may be replaced with other functional groups such as bromide or trialkylstannyl groups. The replacement of the hydrogen atoms may take place using any reaction mechanism suitable for use with heterocyclic ring structures. In an alternate embodiment, the W and/or W' containing derivatives may be formed prior to converting thiophene to the first reaction product (e.g., 3,4-dihydroxythiophene) and then undergoing a reaction procedure shown above for the conversion of 3,4-dihydroxythiophene or 3,4-dihydroxyselenophene derivatives to the imidazolone, dioxolone, imidazolethione or dioxolethione based monomers where the W and W' are compatible with the chemistry outlined above.

EXAMPLES

The following examples are provided to illustrate various embodiments and comparisons and are not intended to restrict the scope of the disclosure. The structure of the compounds formed by the following Examples was confirmed by using NMR in accordance with conventional methods.

Example 1

The compound selenolo[2,3-c]thiophene was prepared in a single reaction mixture in accordance with the method of the present disclosure.

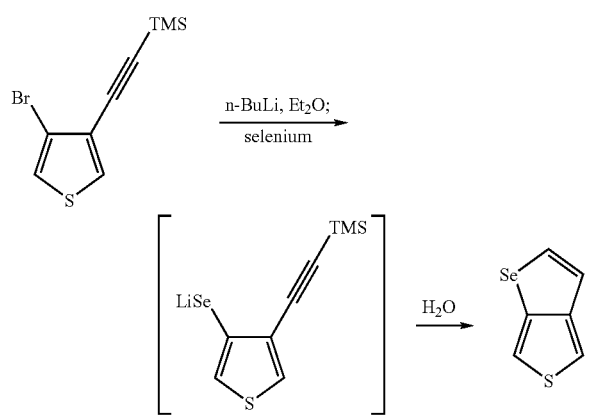

A solution of 2-bromomethyl-4-trimethylsilanyl-but-1-en-3-yne-1-thiol (5.00 g, 19.3 mmol) in ether (19.3 mL) under $N_2$ was cooled to −80° C. Maintaining the temperature below −50° C., n-butyl lithium (2.5 M in hexanes, 7.60 mL, 19.3 mmol) was added. The reaction was allowed to warm to −20° C. and then was cooled to −30° C. Selenium powder (1.60 g, 20.3 mmol) was added in one portion and stirred at −5° C. for 1 h. The reaction was cooled to −30° C., water (19.3 mL) was added, and the mixture was agitated vigorously for 20 seconds. The phases were split immediately. The ether layer was extracted with cold water (5.00 mL). The aqueous layers were combined and heated to 70° C. for 1.5 h. Upon cooling to room temperature the reaction mixture was extracted with MTBE (3×20.0 mL). The combined MTBE extracts were dried over magnesium sulfate and concentrated to an oil. The crude oil was purified by column chromatography (silica gel, cyclohexane) to provide selenolo[2,3-c]thiophene as an oil (2.30 g, 12.3 mmol, 63.7 mol %): 500 MHz $^1$H NMR (DMSO-$d_6$) δ 7.96 (d, J=6.0 Hz, 1H), 7.69 (d, J=2.6 Hz, 1H), 7.61 (dd, J=2.7, 0.6 Hz, 1H), 7.25 (d, J=6.0 Hz, 1H); 125 MHz $^{13}$C NMR (DMSO-$d_6$) δ 149.6, 135.4, 133.5, 120.2, 115.1, 114.8; 76 MHz $^{77}$Se NMR (DMSO-$d_6$) δ 429.3 (dd, J{$^{77}$Se-$^1$H}=47.0, 7.6 Hz); UV-Vis $\lambda_{max}$=243.9 nm ($CH_2Cl_2$); IR (ATR) v 3096, 1548, 1483, 1422, 1340, 1278, 1169, 1070, 982, 834, 758, 726 cm$^{-1}$; MS (+APCI) m/z (M+1)=189.

Example 2

The compound selenolo[3,4-b]selenophene was prepared in a series of reactions in accordance with the method of the present disclosure.

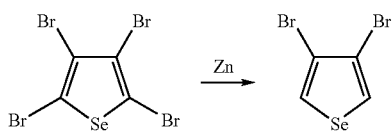

To a stirred slurry of 2,3,4,5-tetrabromo-selenophene (6.20 g, 13.9 mmol) in acetic acid (10.0 mL) and water (20.0 mL) under $N_2$ was added zinc (2.90 g, 45.1 mmol). The mixture was heated to 100° C. for 3 h. The reaction mixture was extracted with MTBE. The MTBE extracts were quenched with saturated sodium bicarbonate until the pH was 7-8. The organic was dried over sodium sulfate, filtered, and concentrated to an oil. The crude oil was purified by column chromatography (silica gel, heptane) to provide 3,4-dibromo-selenophene (1.95 g, 6.75 mmol, 48.6 mol %): 500 MHz $^1$H NMR (CDCl$_3$) δ 7.93 (s, 2H); 125 MHz $^{13}$C NMR (CDCl$_3$) δ 127,114.

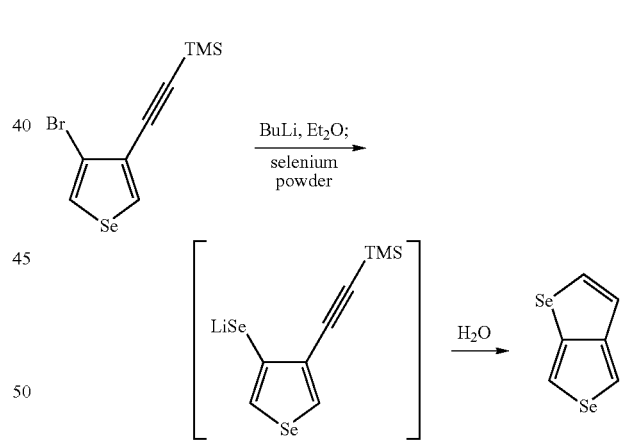

To a pressure vessel purged with $N_2$ was added 3,4-dibromo-selenophene (3.69 g, 12.77 mmol), DMF (10.0 mL), triphenylphosphine (0.669 g, 2.55 mmol), copper(I) iodide (0.161 g, 0.843 mmol), diethylamine (dried over KOH, 20.0 mL, 191.55 mmol), (trimethylsilyl)acetylene (0.910 mL, 6.39 mmol), and palladium dichloride-bis-triphenylphosphine (0.592 g, 0.843 mmol). The reaction vessel was sealed and the mixture heated to 90° C. for 1 h. Upon cooling to room temperature, the reaction mixture was diluted with MTBE (100.0 mL) and was washed with 0.1 M HCl (3×50.0 mL). The combined aqueous layers were extracted with MTBE (50.0 mL). The combined MTBE extracts were quenched with saturated sodium bicarbonate (50.0 mL), dried over magnesium sulfate, and concentrated to an oil. The crude oil was purified by column chromatography (silica gel, cyclohexane) to provide (4-Bromo-selenophen-3-ylethynyl)-trimethyl-silane (1.55 g, 5.08 mmol, 79.5 mol %): 500 MHz $^1$H NMR (CDCl$_3$) δ 8.15 (d, J =2.9 Hz, 1 H), 7.58 (d, J =2.9 Hz, 1 H), 0.26 (S, 9h); 125 MHz $^{13}$C NMR (CDCl$_3$) δ 135.4, 127.0, 126.4, 114.1, 99.8, 96.8, 0.2.

A solution of (4-bromo-selenophen-3-ylethynyl)-trimethyl-silane (1.51 g, 4.95 mmol) in ether (6.00 mL) under $N_2$ was cooled to −65° C. Maintaining the temperature above −50° C., n-butyl lithium (2.5 M in hexanes, 1.98 mL, 4.99 mmol) was added. The reaction was allowed to warm to −20° C., and then was cooled back to −30° C. Selenium powder (0.410 g, 5.20 mmol) was added in one portion and stirred at −5° C. for 1 h. The reaction was cooled to −30° C., water (6.00 mL) was added, and the mixture was agitated vigorously for 20 seconds. The phases were split immediately. The ether layer was extracted with cold water (6.00 mL). The aqueous layers were combined and heated to 70° C. for 1 h. Upon cooling to room temperature the reaction was extracted with MTBE (2×20.0 mL). The combined MTBE extracts were dried over magnesium sulfate and concentrated to an oil. The crude oil was purified by column chromatography (silica gel, cyclohexane; and 4:1 cyclohexane/pentane). The crude material was recrystallized from pentane to provide Selenolo[3,4-b]selenophene as an off-white solid (0.127 g, 0.543 mmol, 11.0 mol %): 500 MHz $^1$H NMR (DMSO-$d_6$) δ 8.29 (d, J=2.3 Hz, 1H), 8.17 (dd, J=2.2, 0.6 Hz, 1 H), 8.02 (d, J=6.0 Hz, 1 H), 7.11 (d, J=6.0 Hz, 1 H); 125 MHz $^{13}$C NMR (DMSO-$d_6$) δ 152.0, 136.4, 132.7, 121.3, 120.8, 119.5; 76 MHz $^{77}$Se NMR (DMSO-$d_6$) δ 734.5 (t, J{$^{77}$Se-$^1$H}=46.5 Hz), 429.3 (dd, J{$^{77}$Se-$^1$H}=46.4, 7.1 Hz); UV-Vis $\lambda_{max}$=249.5 nm (MeOH); IR (ATR) ν 3100, 1548, 1493, 1437, 1318, 1272, 1152, 1108, 1067, 967, 895, 756, 730 cm$^{-1}$; MS (+APCl) m/z(M+1)=237.

Example 3

The compound selenolo[3,4-b]thiophene was prepared in a series of reactions in accordance with the method of the present disclosure.

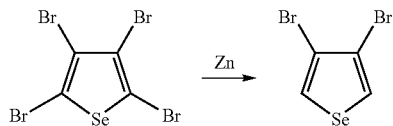

To a stirred slurry of 2,3,4,5-tetrabromo-selenophene (6.20 g, 13.9 mmol) in acetic acid (10.0 mL) and water (20.0 mL) under N$_2$ was added zinc (2.90 g, 45.1 mmol). The mixture was heated to 100° C. for 3 h. The reaction mixture was extracted with MTBE. The MTBE extracts were quenched with saturated sodium bicarbonate until the pH was 7-8. The organic was dried over sodium sulfate, filtered, and concentrated to an oil. The crude oil was purified by column chromatography (silica gel, heptane) to provide 3,4-dibromo-selenophene (1.95 g, 6.75 mmol, 48.6 mol %): 500 MHz $^1$H NMR (CDCl$_3$) δ 7.93 (s, 2H); 125 MHz $^{13}$C NMR (CDCl$_3$) δ 127, 114.

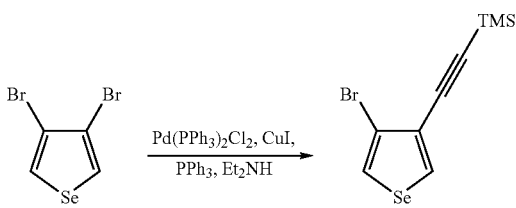

To a pressure vessel purged with N$_2$ was added 3,4-dibromo-selenophene (3.69 g, 12.77 mmol), DMF (10.0 mL), triphenylphosphine (0.669 g, 2.55 mmol), copper(I) iodide (0.161 g, 0.843 mmol), diethylamine (dried over KOH, 20.0 mL, 191.55 mmol), (trimethylsilyl)acetylene (0.910 mL, 6.39 mmol), and palladium dichloride-bis-triphenylphosphine (0.592 g, 0.843 mmol). The reaction vessel was sealed and the mixture heated to 90° C. for 1 h. Upon cooling to room temperature, the reaction mixture was diluted with MTBE (100.0 mL) and was washed with 0.1 M HCl (3×50.0 mL). The combined aqueous layers were extracted with MTBE (50.0 mL). The combined MTBE extracts were quenched with saturated sodium bicarbonate (50.0 mL), dried over magnesium sulfate, and concentrated to an oil. The crude oil was purified by column chromatography (silica gel, cyclohexane) to provide (4-bromo-selenophen-3-ylethynyl)-trimethyl-silane (1.55 g, 5.08 mmol, 79.5 mol %): 500 MHz $^1$H NMR (CDCl$_3$) δ 8.15 (d, J=2.9 Hz, 1H), 7.58 (d, J=2.9 Hz, 1H), 0.26 (S, 9h); 125 MHz $^{13}$C NMR (CDCl$_3$) δ 135.4, 127.0, 126.4, 114.1, 99.8, 96.8, 0.2.

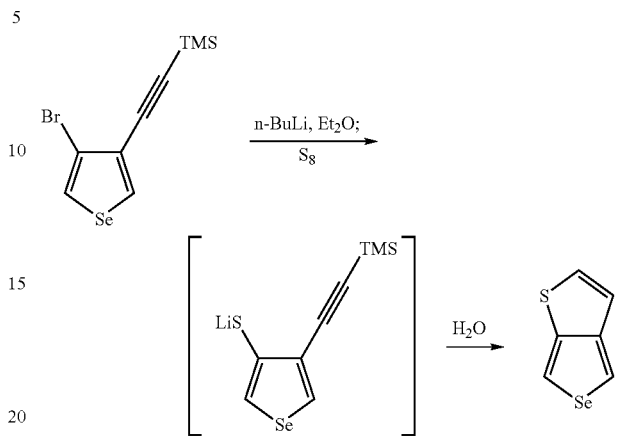

A solution of (4-bromo-selenophen-3-ylethynyl)-trimethyl-silane (R=TMS, 1.90 g, 6.23 mmol) in ether (7.40 mL) under N$_2$ was cooled to −70° C. Maintaining the temperature below −50° C., n-butyl lithium (2.5 M in hexanes, 2.50 mL, 6.23 mmol) was added. The reaction was allowed to warm to −20° C. and then cooled back to −30° C. Sulfur (0.210 g, 6.54 mmol) was added in one portion and stirred at 0° C. for 1 h. The reaction was cooled to −30° C.; water (7.40 mL) was added and agitated vigorously for 20 seconds. The phases were split immediately. The ether layer was extracted with cold water (4.00 mL). The aqueous layers were combined and heated to 70 ° C. for 1.5 h. Upon cooling to room temperature the reaction was extracted with MTBE (3×20.0 mL). The combined MTBE extracts were dried over magnesium sulfate and concentrated to an oil. The crude oil was purified by column chromatography (silica gel, cyclohexane) to provide selenolo[3,4-b]thiophene as an oil (0.344 g, 1.84 mmol, 29.5 mol %): 500 MHz $^1$H NMR (DMSO-$d_6$) δ 8.24 (d, J=2.3 Hz, 1H), 8.18 (dd, J=2.3, 0.8 Hz, 1H), 7.68 (d, J=5.7 Hz, 1 H), 6.88 (d, J=5.7 Hz, 1 H); 125 MHz $^{13}$C NMR (DMSO-$d_6$) δ 149.7, 140.0, 133.0, 119.0, 117.4, 116.4; 76 MHz $^{77}$Se NMR (DMSO-$d_6$) δ 739.7 (t, J{$^{77}$Se-$^1$H}=46.6 Hz); UV-Vis $\lambda_{max}$=248.3 nm (CH$_2$Cl$_2$); IR (ATR) ν 3095, 1549, 1488, 1319, 1289, 1152, 1077, 989, 804, 748 cm$^{-1}$; MS (+APCl) m/z(M+1)=189.

Example 4

The monomers can be readily derivatised in the 2-position according to the disclosure providing new compositions of matter. This example illustrates the preparation of 2-phenyl-selenolo[3,4-b]selenophene, which was prepared in a series of reactions in accordance with the method of the present disclosure.

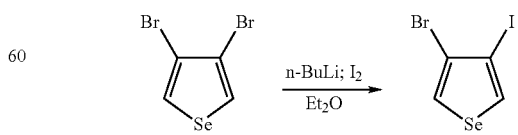

A solution of 3,4-dibromo-selenophene (2.36 g, 8.17 mmol) in ether (24.0 mL) under N$_2$ was cooled to −70° C. Maintaining the temperature below −50° C. n-butyl lithium (2.5 M in hexanes, 3.43 mL, 8.58 mmol) was added. Iodine chips (2.28 g, 8.99 mmol) were added and the reaction mixture was warmed to 0° C. over at least 1 h. After addition of MTBE (50.0 mL), the reaction was quenched with saturated sodium bicarbonate (20.0 mL). The phases were split and the MTBE/ether extract was quenched with additional saturated sodium bicarbonate (20.0 mL). The combined MTBE/ether extracts were dried over magnesium sulfate and concentrated to an oil. The oil was purified by column chromatography (silica gel, cyclohexane). The combined fractions in cyclohexane were treated with sodium metabisulfite, filtered, and concentrated to provide 3-bromo-4-iodo-selenophene as an oil (1.97 g, 5.87 mmol, 71.8 mol %): 300 MHz $^1$H NMR (CDCl$_3$) δ 8.1 (d, J=3.0 Hz, 1H), 7.89 (d, J=3.0 Hz, 1H).

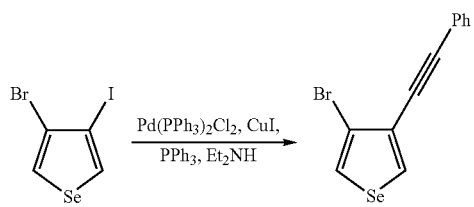

To a pressure vessel purged with N$_2$ was added 3-bromo-4-iodo-selenophene (1.97 g, 5.87 mmol), DMF (5.20 mL), triphenylphosphine (0.307 g, 1.17 mmol), copper(I) iodide (0.0740 g, 0.387 mmol), diethylamine (dried over KOH, 9.20 mL, 88.0 mmol), phenyl acetylene (0.645 mL, 5.87 mmol), and palladium dichloride-bis-triphenylphosphine (0.272 g, 0.387 mmol). The reaction vessel was sealed and the mixture heated to 70° C. for 1 h. Upon cooling to room temperature, the reaction mixture was diluted with MTBE (50.0 mL) and was washed with 0.1 M HCl (3×30.0 mL). The combined aqueous layers were extracted with MTBE (30.0 mL). The MTBE rich layer was dried over magnesium sulfate and concentrated to an oil. The crude oil was purified by column chromatography (silica gel, cyclohexane) to provide 3-bromo-4-phenylethynyl-selenophene (1.07 g, 3.19 mmol, 54.3 mol %): 500 MHz $^1$H NMR (CDCl$_3$) δ 8.18 (d, J=2.9 Hz, 1H), 7.90 (d, J=2.9 Hz, 1H), 7.58-7.54 (m, 2H), 7.36-7.32 (m, 3H); 125 MHz $^{13}$C NMR (CDCl$_3$) δ 134.2, 131.7, 128.5, 128.4, 126.8, 126.3, 122.9, 114.1, 91.0, 84.7.

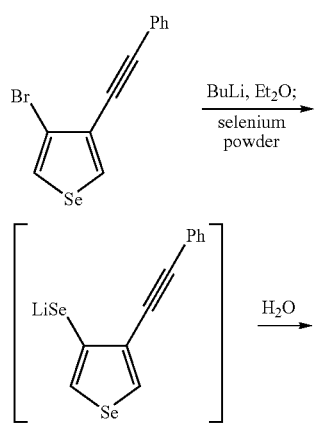

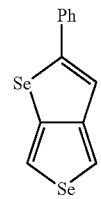

A solution of 3-bromo-4-phenylethynyl-selenophene (2.00 g, 6.45 mmol) in ether (26.0 mL) under N$_2$ was cooled to −65° C. Maintaining the temperature below −50° C. tert-butyl lithium (1.7 M in pentane, 7.59 mL, 12.9 mmol) was added. The reaction was stirred at −60 to −50° C. for 0.5 h. Selenium powder (0.530 g, 6.71 mmol) was added in one portion; the mixture was allowed to warm to room temperature over 2 h and was held for 1 h. The solvent was evaporated and a solution of potassium hydroxide (0.434 g, 7.74 mmol) in methanol (25.0 mL) was added and heated to reflux for 15 h. Upon cooling to room temperature the reaction was concentrated to an oil, dissolved in CH$_2$Cl$_2$ and extracted with water. The aqueous layer was extracted with CH$_2$Cl$_2$. The combined organic layers were dried over magnesium sulfate and concentrated to a crude residue. The crude material was recrystallized from CH$_2$Cl$_2$ and methanol to provide 2-phenyl-selenolo[3,4-b]selenophene as a light orange powder (0.571 g, 1.84 mmol, 40.8 mol %): 500 MHz $^1$H NMR (DMSO-d$_6$) δ 8.34 (d, J=2.3 Hz, 1H), 8.22 (dd, J=2.2, 0.6 Hz, 1H), 7.62-7.59 (m, 2H), 7.57 (s, 1H), 7.45-7.42 (m, 2H), 7.39-7.35 (m, 1H); 125 MHz $^{13}$C NMR (DMSO-d$_6$) δ 151.9, 148.3, 136.0, 134.6, 129.1, 128.5, 125.9, 122.6, 119.9, 116.9; 95 MHz $^{77}$Se NMR (DMSO-d$_6$) δ 731.2 (t, J$\{^{77}$Se-$^1$H$\}$=45.8 Hz), 427.7 (d, J$\{^{77}$Se-$^1$H$\}$=3.8 Hz); UV-Vis λ$_{max}$=309.3 nm (CH$_2$Cl$_2$); IR (ATR) ν 3088, 1553, 1482, 1438, 1327, 1303, 1221, 1152, 1074, 1028, 901, 843, 827, 750, 683 cm$^{-1}$; MS (+APCI) m/z(M+1)=313.

Example 5

The monomers can be readily derivatised in the 2-position according to the disclosure providing new compositions of matter. This example illustrates the preparation of 2-phenyl-selenolo[3,4-b]thiophene, which was prepared in a series of reactions in accordance with the method of the present disclosure.

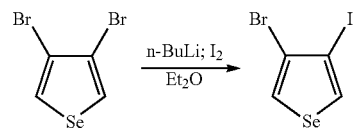

A solution of 3,4-dibromo-selenophene (2.36 g, 8.17 mmol) in ether (24.0 mL) under N$_2$ was cooled to −70 ° C. Maintaining the temperature below −50° C. n-butyl lithium (2.5 M in hexanes, 3.43 mL, 8.58 mmol) was added. Iodine chips (2.28 g, 8.99 mmol) were added and the reaction mixture was warmed to 0° C. over at least 1 h. After addition of MTBE (50.0 mL), the reaction was quenched with saturated sodium bicarbonate (20.0 mL). The phases were split and the MTBE/ether extract was quenched with additional saturated sodium bicarbonate (20.0 mL). The combined MTBE/ether extracts were dried over magnesium sulfate and concentrated to an oil. The oil was purified by column chromatography (silica gel, cyclohexane). The combined fractions in cyclohexane were treated with sodium metabisulfite, filtered, and concentrated to provide 3-bromo-4-iodo-selenophene as an oil (1.97 g, 5.87 mmol, 71.8 mol %): 300 MHz $^1$H NMR (CDCl$_3$) δ 8.1 (d, J=3.0 Hz, 1H), 7.89 (d, J=3.0 Hz, 1H).

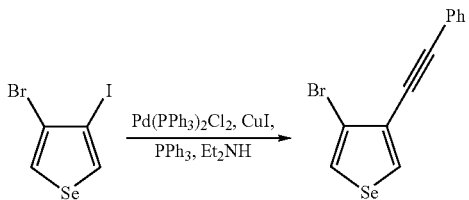

To a pressure vessel purged with N$_2$ was added 3-bromo-4-iodo-selenophene (1.97 g, 5.87 mmol), DMF (5.20 mL), triphenylphosphine (0.307 g, 1.17 mmol), copper(I) iodide (0.0740 g, 0.387 mmol), diethylamine (dried over KOH, 9.20 mL, 88.0 mmol), phenyl acetylene (0.645 mL, 5.87 mmol), and palladium dichloride-bis-triphenylphosphine (0.272 g, 0.387 mmol). The reaction vessel was sealed and the mixture heated to 70° C. for 1 h. Upon cooling to room temperature, the reaction mixture was diluted with MTBE (50.0 mL) and was washed with 0.1 M HCl (3×30.0 mL). The combined aqueous layers were extracted with MTBE (30.0 mL). The MTBE rich layer was dried over magnesium sulfate and concentrated to an oil. The crude oil was purified by column chromatography (silica gel, cyclohexane) to provide 3-bromo-4-phenylethynyl-selenophene (1.07 g, 3.19 mmol, 54.3 mol %): 500 MHz $^1$H NMR (CDCl$_3$) δ 8.18 (d, J=2.9 Hz, 1H), 7.90 (d, J=2.9 Hz, 1H), 7.58-7.54 (m, 2H), 7.36-7.32 (m, 3H); 125 MHz $^{13}$C NMR (CDCl$_3$) δ 134.2, 131.7, 128.5, 128.4, 126.8, 126.3, 122.9, 114.1, 91.0, 84.7.

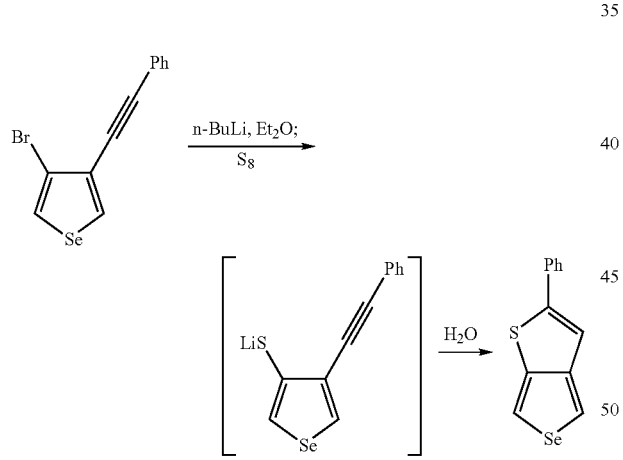

A solution of 3-bromo-4-phenylethynyl-selenophene (1.65 g, 5.32 mmol) in ether (6.00 mL) under N$_2$ was cooled to −70° C. Maintaining the temperature below −50° C., n-butyl lithium (2.5 M in hexanes, 2.13 mL, 5.32 mmol) was added. The reaction was allowed to warm to −30° C. and then was cooled to −50° C. Sulfur (0.179 g, 5.59 mmol) was added in one portion and stirred at 0° C. for 2 h. The solvent was evaporated and a solution of KOH (0.373 g, 6.65 mmol) in methanol (6 mL) was added and heated to reflux for 19 h. Upon cooling to room temperature, the reaction was concentrated, reconstituted in CH$_2$Cl$_2$ and washed with water. The CH$_2$Cl$_2$ layer was treated with magnesium sulfate and Darco G60. After filtration and addition of methanol, the CH$_2$Cl$_2$ was evaporated until the material crystallized out of solution.

The crude material was recrystallized from CH$_2$Cl$_2$/methanol to obtain 2-phenyl-selenolo[3,4-b]thiophene as a light brown solid (0.355 g, 1.35 mmol, 25.4 mol %): 500 MHz $^1$H NMR (DMSO-d$_6$) δ 8.29 (d, J=2.1 Hz, 1H), 8.22 (d, J=1.8 Hz, 1H), 7.68 (d, J=7.3 Hz, 2H), 7.46 (t, J=7.3 Hz, 2H), 7.40-7.37 (m, 2H); 125 MHz $^{13}$C NMR (DMSO-d$_6$) δ 149.8, 148.0, 138.4, 134.3, 129.1, 128.7, 125.5, 120.1, 116.8, 113.7; 95 MHz $^{77}$Se NMR (DMSO-d$_6$) δ 737.2 (t, J {$^{77}$Se-$^1$H}=45.8 Hz); UV-Vis λ$_{max}$=308.2 nm (CH$_2$Cl$_2$); IR (ATR) ν 3092, 1552, 1484, 1440, 1329, 1224, 1152, 1069, 1027, 924, 903, 819, 752, 735, 685 cm$^{-1}$; MS (+APCl) m/z (M+1)=265.

Example 6

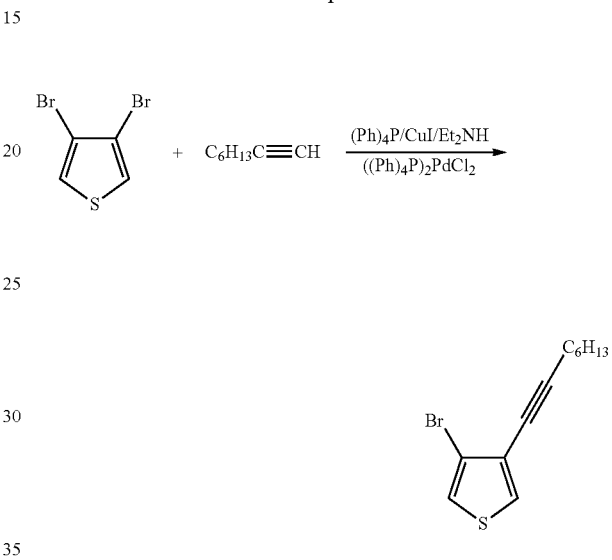

Into a 250 mL 4 necked RB flask equipped with a magnetic stirring bar, thermometer, rubber septum, argon inlet and reflux condenser with argon outlet (tubed to a silicon oil bubbler) is added 59.4 g (246 mmol) of 3,4-dibromothiophene, 44.0 g of diethylamine, 27.0 g (245 mmol) of 1-octyne, 148 mg of triphenylphosphine, 106 mg of copper iodide and 295 mg dichlorobis(triphenylphosphine) palladium(II). The mixture is heated with a silicon oil bath to 60° C. under argon with stirring for 40 hrs. The cooled mixture is then concentrated on a rotary evaporator at reduced pressure and the residue taken up in 200 mL of pentane and washed with 2×25 mL of water and the pentane phase dried over sodium sulfate and then concentrated on a rotary evaporator. The residue is then distilled at 55-60 ° C. and 0.40 torr to remove 2.3 g of unreacted 3,4-dibromothiophene. The residue was chromatographed through silica gel eluting with hexanes to yield 17.1 g of 3-bromo-4(oct-1-ynyl)thiophene as a light yellow-orange oil which was used directly to prepare 2-hexylselenolo[2,3-c]thiophene.

Example 7

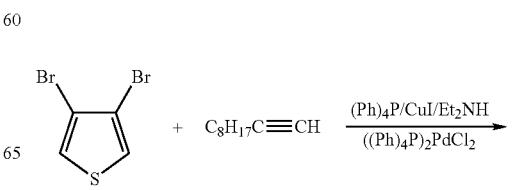

27
-continued

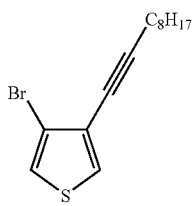

Into a 250 mL 4 necked RB flask equipped with a magnetic stirring bar, thermometer, rubber septum, argon inlet and reflux condenser with argon outlet (tubed to a silicon oil bubbler) is added 59.88 g (247 mmol) of 3,4-dibromothiophene, 44.0 g of diethylamine, 34.2 g (247 mmol) of 1-decyne, 149 mg of triphenylphosphine, 107 mg of copper iodide and 204 mg dichlorobis(triphenylphosphine) palladium(II). The mixture is heated with a silicon oil bath to 60° C. under argon with stirring for 40 hrs. The cooled mixture is then concentrated on a rotary evaporator at reduced pressure and the residue taken up in 200 mL of pentane and washed with 2×25 mL of water and the pentane phase dried over sodium sulfate and then concentrated on a rotary evaporator. The residue is then distilled at 60-65° C. and 0.35 torr to remove 18 g of unreacted 3,4-dibromothiophene. The residue was chromatographed through silica gel eluting with hexanes to yield 37.7g of compound 3-Bromo-4(dec-1-ynyl)thiophene as a light yellow-orange oil which was used directly to prepare compound 2-octylselenolo[2,3-c]thiophene.

Example 8

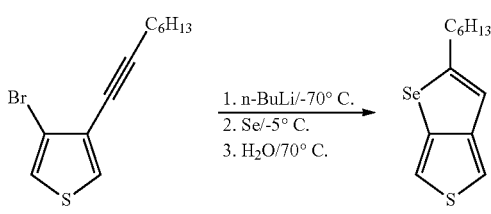

Into a 250 mL 4 necked RB flask equipped with a magnetic stirring bar, thermometer, rubber septum, argon inlet and argon outlet (tubed to a silicon oil bubbler) is added 17.1 g (0.063 moles) of 3-bromo-4-(oct-1-ynyl)thiophene via syringe and 100 mL of anhydrous ether via cannula. Under argon and with stirring the mixture is cooled to −70° C. and 24 mL of 2.5 M n-butyllithium in hexanes is added via syringe. After 30 minutes 6.0 g (0.076 moles) of selenium is added all at once and the reaction allowed to warm to −30° C. The mixture is held at −5° C. for 30 minutes and then 100 ml of saturated aqueous sodium chloride is added maintaining the temperature below −5° C. The mixture is then phase separated in a separatory funnel and an additional 30 mL of saturated aqueous salt solution is added to the organic phase, The two salt solutions are then added to a 250 mL 4 necked RB flask equipped with a magnetic stirring bar, thermometer, rubber septum, argon inlet and argon outlet (tubed to a silicon oil bubbler) and heated to 60° C. with stirring and under argon in a preheated silicon oil bath for 1 hour. The cooled mixture is then extracted with 2×200 mL of pentane. The organic phase is then dried over sodium sulfate and the solvents removed on a rotary evaporator. The residue was chromatographed on silica gel eluting with hexanes to yield 7.49 g of 2-hexyselenolo[2,3-c]thiophene as a light yellow-orange oil of 96% purity by gc-fid area. This material was used directly to prepare compound dibromo-2-hexylselenolo[2,3-c]thiophene.

Example 9

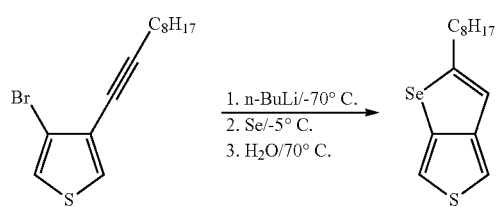

Into a 250 mL 4 necked RB flask equipped with a magnetic stirring bar, thermometer, rubber septum, argon inlet and argon outlet (tubed to a silicon oil bubbler) is added 17.1 g (0.574 moles) of 3-bromo-4(dec-1-ynyl)thiophene via syringe and 100 mL of anhydrous ether via cannula. Under argon and with stirring the mixture is cooled to −70° C. and 24 mL of 2.5 M n-butyllithium in hexanes is added via syringe. After 30 minutes 5.81 g (0.735 moles) of selenium is added all at once and the reaction allowed to warm to −30° C. The mixture is held at −5° C. for 30 minutes and then 100 ml of saturated aqueous salt sodium chloride is added maintaining the temperature below −5° C. The mixture is then phase separated in a separatory funnel and an additional 30 mL of saturated aqueous salt solution is added to the organic phase, The combined salt solutions are then added to a 250 mL 4 necked RB flask equipped with a magnetic stirring bar, thermometer, rubber septum, argon inlet and argon outlet (tubed to a silicon oil bubbler) and heated to 70° C. with stirring and under argon in a preheated silicon oil bath for 1 hour. The cooled mixture is then extracted with 3×300 mL of pentane. The mixture is then dried over sodium sulfate and the solvents are removed on a rotary evaporator The residue was chromatographed on silica gel eluted with hexanes. The hexanes were removed on a rotary evaporator at reduced pressure to give 11.6 g of 2-octylselenolo[2,3-c]thiophene as a light yellow oil with a purity of 98.1% by gc-fid area.

Example 10

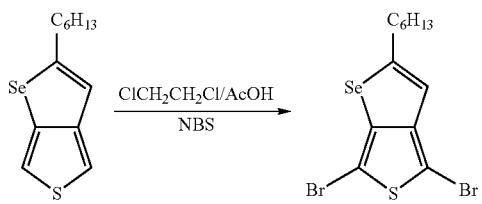

Add 0.90 g (3.3 mmol) of compound 2-hexylselenolo[2,3-c]thiophene to 15 mL of dichloromethane in a 100 mL 4 necked RB flask equipped with a magnetic stirring bar, rubber septum, thermometer, argon inlet and outlet (plumbed to a silicone oil bubbler with Tygon), and a pressure equalizing dropping funnel. With stirring and under argon a solution of 1.18 g (6.6 mmol) of N-bromosuccinimide in 40 mL of dichloromethane is added dropwise over a period of 30 minutes from the addition funnel to the solution which is cooled in an ice/water bath to maintain the reaction at <10° C. After stirring at ambient temperature for 2 hours the solvent was removed on a rotary evaporator at reduced pressure and the residue chromatographed on silica gel eluted with hexanes to give 1.5 g of dibromo-2-hexylselenolo[2,3-c]thiophene as a yellow-orange solid with 98.5% purity by gc-fid area.

Example 11

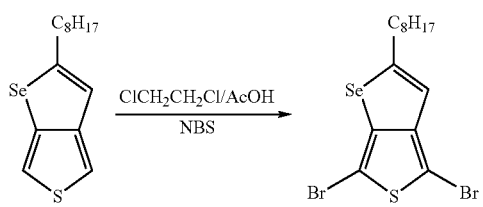

Add 0.8 g (2.7 mmol) of 2-octylselenolo[2,3-c]thiophene to 25 mL of dichloromethane in a 50 mL 4 necked RB flask equipped with a magnetic stirring bar, rubber septum, thermometer, argon inlet and outlet (plumbed to a silicone oil bubbler with Tygon), and a pressure equalizing dropping funnel. With stirring and under argon a solution of 0.91 g (5.1 mmol) of N-bromosuccinimide in 10 mL of dichloromethane is added dropwise over a period of 30 minutes to the solution which is cooled in an ice/water bath to maintain the reaction at <10° C. After stirring for 5 hrs at ambient temperature, the final reaction mass is concentrated on a rotary evaporator and the residue passed through a short pad of silica gel with hexanes. The eluant is evaporated to dryness on a rotary evaporator to give 0.94 g of dibromo-2-octylselenolo[2,3-c]thiophene as a light yellow solid determined to be 99.6% pure by gc-fid area.

Example 12

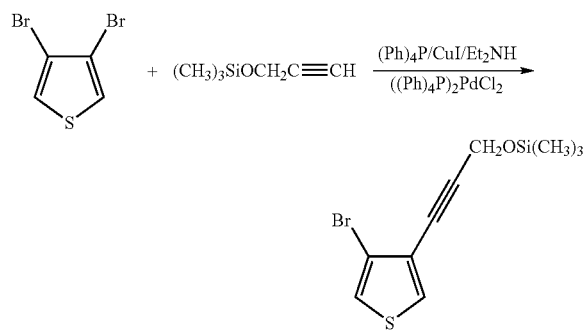

Into a 250 mL 4 necked RB flask equipped with a magnetic stirring bar, thermometer, rubber septum, argon inlet and reflux condenser with argon outlet (tubed to a silicon oil bubbler) is added 48.3 g (229 mmol) of 3,4-dibromothiophene, 13.0 g of triethylamine, 20.1 g (157 mmol) of 3-trimethylsiloxypropyne, 130 mg of triphenylphosphine, 147 mg of copper iodide and 470 mg of dichlorobis(triphenylphosphine) palladium(II). The mixture is heated with a silicon oil bath to 70° C. under argon with stirring for 5.5 hrs. The cooled mixture is then concentrated on a rotary evaporator at reduced pressure and the residue taken up in 200 mL of hexanes and washed with 2×25 mL of water and the pentane phase dried over sodium sulfate and then concentrated on a rotary evaporator. The residue was chromatographed through neutral silica gel eluted with 2/1 methylene chloride/ethyl acetate to yield 8.9 g of 3-bromo-4(trimethylsiloxypropynyl) thiophene as a light yellow oil which was used directly to prepare 2-hydroxymethylselenolo[2,3-c]thiophene.

Example 13

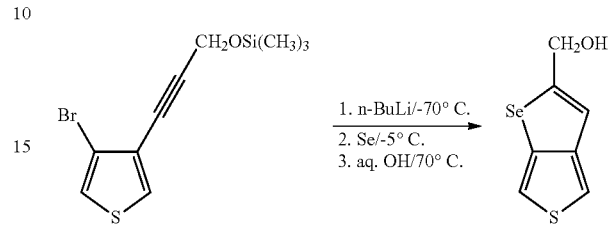

Into a 250 mL 4 necked RB flask equipped with a magnetic stirring bar, thermometer, rubber septum, argon inlet and argon outlet (tubed to a silicon oil bubbler) is added 8.9 g (0.031 moles) of 3-bromo-4-(trimethylsiloxypropynyl) thiophene via syringe and 100 mL of anhydrous ether via cannula. Under argon and with stirring the mixture is cooled to −70° C. and 13 mL of 2.5 M n-butyllithium in hexanes is added via syringe. After 30 minutes 3.9 g (0.035 moles) of selenium is added all at once and the reaction allowed to warm to −30° C. The mixture is held at <10° C. for 30 minutes and then 100 ml of saturated aqueous sodium chloride is added. The mixture is then phase separated in a separatory funnel and an additional 30 mL of saturated aqueous salt solution is added to the organic phase, The two salt solutions are then added to a 250 mL 4 necked RB flask equipped with a magnetic stirring bar, thermometer, rubber septum, argon inlet and argon outlet (tubed to a silicon oil bubbler) and heated to 60° C. with stirring and under argon in a preheated silicon oil bath for 35 minutes. The cooled mixture is then extracted with 2×100 mL of methylene chloride The organic phase is then dried over sodium sulfate and the solvent removed on a rotary evaporator. The residue was chromatographed on silica gel eluted with 9/1 methylene chloride/ethyl acetate to yield 2.5 g of 2-hydroxymethylselenolo[2,3-c]thiophene as a light yellow-solid of 99.1% purity by gc-fid area.

Example 14

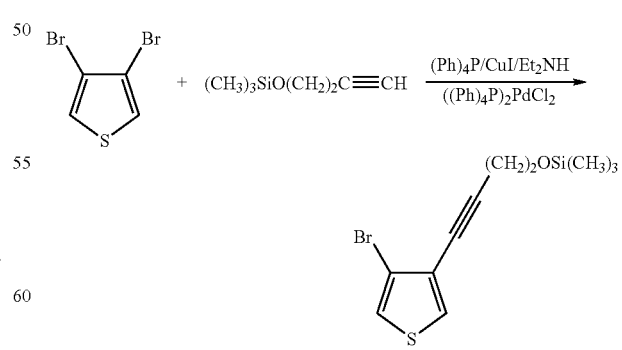

Into a 250 mL 4 necked RB flask equipped with a magnetic stirring bar, thermometer, rubber septum, argon inlet and reflux condenser with argon outlet (tubed to a silicon oil bubbler) is added 55.0 g (229 mmol) of 3,4-dibromothiophene, 15.6 g of triethylamine, 9.75 g (68.5 mmol) of trimethylsiloxy-1-butyne, 170 mg of triphenylphosphine, 140 mg of copper iodide and 490 mg of dichlorobis(triphenylphosphine) palladium(II). The mixture is heated with a silicon oil bath to 60° C. under argon with stirring for 2 hrs. The cooled mixture is then concentrated on a rotary evaporator at reduced pressure and the residue taken up in 200 mL of hexanes and washed with 2×25 mL of water and the pentane phase dried over sodium sulfate and then concentrated on a rotary evaporator. The residue was chromatographed through neutral silica gel eluted with 2/1 methylenechloride/hexanes to yield 4.8 g of 3-bromo-4(trimethylsiloxybutynyl)thiophene as a light yellow oil which was used directly to prepare 2-hydroxyethylselenolo[2,3-c]thiophene.

Example 15

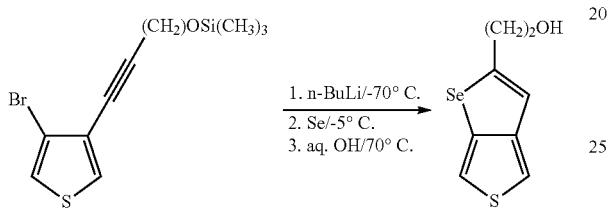

Into a 250 mL 4 necked RB flask equipped with a magnetic stirring bar, thermometer, rubber septum, argon inlet and argon outlet (tubed to a silicon oil bubbler) is added 11.6 g (0.040 moles) of 3-bromo-4-(trimethylsiloxybutynyl)thiophene via syringe and 120 mL of anhydrous ether via cannula. Under argon and with stirring the mixture is cooled to −70° C. and 16 mL of 2.5 M n-butyllithium in hexanes is added via syringe. After 30 minutes 3.9 g (0.049 moles) of selenium is added all at once and the reaction allowed to warm to −30° C. The mixture is held at −5° C. for 30 minutes and then 100 ml of saturated aqueous sodium chloride is added maintaining the temperature below −5° C. The mixture is then phase separated in a separatory funnel and an additional 30 mL of saturated aqueous salt solution is added to the organic phase, The two salt solutions are then added to a 250 mL 4 necked RB flask equipped with a magnetic stirring bar, thermometer, rubber septum, argon inlet and argon outlet (tubed to a silicon oil bubbler) and heated to 60° C. with stirring and under argon in a preheated silicon oil bath for 35 minutes. The cooled mixture is then extracted with 2×100 mL of methylene chloride The organic phase is then dried over sodium sulfate and the solvent removed on a rotary evaporator. The residue was chromatographed on silica gel eluted with 9/1 methylene chloride/ethyl acetate to yield 3.72 g of 2-hydroxyethylselenolo[2,3-c]thiophene as a light yellow-solid of 98.1% purity by gc-fid area.

While the disclosure has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to any particular embodiment disclosed as the best mode contemplated for carrying out this invention, but that the invention will include all embodiments falling within the scope of the appended claims.

The invention claimed is:

1. A heterocyclic monomer compound according to the following formula:

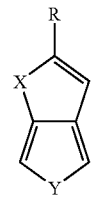

wherein X is Se, Y is S, R is a substituent group selected from the group consisting of hydroxyl, alkyl, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, halogen, nitro, cyano, sulfonic acid, alkyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, and phenyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, in which one or more non-adjacent CH$_2$ groups in alkyl is optionally replaced, independently, with —O—, —S—, —NH—, —NR'—, —CO—, —COO—, —OCO—, —OCO—O—, —S—CO—, —CO—S—, —CH═CH— or —C≡C— in such a manner that O and/or S atoms are not linked directly to one another, each of R' and R", independently, being H, aryl, or alkyl with 1 to 12 C-atoms.

2. The compound of claim 1, wherein R is selected from the group consisting of alkylaryl, arylalkyl, aryl, heteroaryl, C$_1$ to C$_{12}$ primary, secondary or tertiary alkyl groups, optionally mono- or polysubstituted by F, Cl, Br, I or CN, phenyl, substituted phenyl groups, cyclohexyl, naphthalenyl, hydroxyl, alkyl ether, perfluoroaryl, and sulfonic acid, esters of sulfonic acid, SF$_5$, and F.

3. The compound of claim 1, wherein R is selected from the group consisting of phenyl, C$_1$ to C$_{12}$ primary, secondary or tertiary alkyl groups and perfluoroalkyl groups.

4. The compound of claim 1, wherein the compound is selected from the group consisting of 2-phenyl-selenolo[2,3-c]thiophene and 2-hexyl-selenolo[2,3-c]thiophene.

5. A heterocyclic monomer compound according to the following formula:

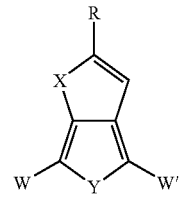

wherein X is Se, Y is S , W' and W is bromine, and

R is selected from the group consisting of hydrogen, hydroxyl, alkyl, arylalkyl, alkenyl, perfluoroalkyl, perfluororaryl, aryl, alkoxy, cycloalkyl, cycloalkenyl, alkanoyl, alklthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, carboxyl, halogen, nitro, cyano, sulfonic acid, alkyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, and phenyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, in which one or more non-adjacent $CH_2$ groups in alkyl is optionally replaced, independently, with —O—, —S—, —NH—, —NR'—, —SiR'R"—, —CO—, —COO—, —OCO—, —OCO—O—, —S—CO—, —CO—S—, —CH=CH— or —C≡C— in such a manner that O and/or S atoms are not linked directly to one another, each of R' and R", independently, being H, aryl, or alkyl with 1 to 12 C-atoms.

6. The compound of claim 5, wherein R is selected from the group consisting of hydrogen, alkylaryl, arylalkyl, aryl, heteroaryl, $C_1$ to $C_{12}$ primary, secondary or tertiary alkyl groups optionally mono- or polysubstituted by F, Cl, Br, I or CN, phenyl, substituted phenyl groups, cyclohexyl, naphthalenyl, hydroxyl, alkyl ether, perfluoroaryl, sulfonic acid, esters of sulfonic acid, $SF_5$, and F.

7. The compound of claim 6, wherein R is selected from the group consisting of phenyl, $C_1$ to $C_{12}$ primary, secondary or tertiary alkyl groups and perfluoroalkyl groups.

8. A method for preparing a compound of formula (1):

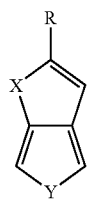

(1)

wherein X is Se, Y is S, R is a substituent group selected from the group consisting of hydroxyl, alkyl, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, halogen, nitro, cyano, sulfonic acid, alkyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, and phenyl substituted with one or more sulfonic acid, esters of sulfonic acid, phosphoric acid, esters of phosphoric acid, carboxylic acid, esters of carboxylic acid, halo, amino, nitro, hydroxyl, cyano and epoxy moieties, in which one or more non-adjacent $CH_2$ groups in alkyl is optionally replaced, independently, with —O—, —S—, —NH—, —NR'—, —CO—, —COO—, —OCO—, —OCO—O—, —S—CO—, —CO—S—, —CH=CH— or —C≡C— in such a manner that O and/or S atoms are not linked directly to one another, each of R' and R", independently, being H, aryl, or alkyl with 1 to 12 C-atoms, the method comprising the steps of:

providing a first reactant having the formula (2):

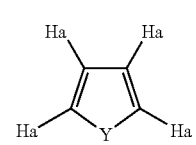

(2)

wherein Ha is bromine;

reducing the first reactant in the presence of a metal reducing agent to form a second reactant having the formula (3):

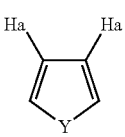

(3)

reacting the second reactant with a substituted 1-alkyne in the presence of a transition metal catalyst to form a third reactant, the third reactant having the formula (4):

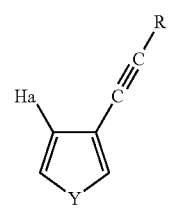

(4)

reacting the third reactant with an alkyl lithium in the presence of a compound comprising X, X being defined above, to produce a fourth reactant having the formula (5):

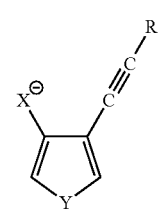

(5)

and reacting the fourth reactant with water to form the compound having formula (1).

9. The method of claim 1, wherein R is selected from the group consisting of hydroxyl, alkyl, arylalkyl, alkenyl, perfluoroalkyl, perfluororaryl, aryl, alkoxy, cycloalkyl, cycloalkenyl, alkanoyl, alkylthio, aryloxy, alkylthioalkyl, alkynyl, alkylaryl, arylalkyl, amido, alkylsulfinyl, alkoxyalkyl, alkylsulfonyl, aryl, arylamino, diarylamino, alkylamino, dialkylamino, arylarylamino, arylthio, heteroaryl, arylsulfinyl, alkoxycarbonyl, arylsulfonyl, halogen, nitro, cyano, sulfonic acid, alkyl substituted with one or more sulfonic acid, sulfonic acid ester, phosphoric acid, phosphoric acid ester, carboxylic acid, carboxylic acid ester, halo, amino, nitro, hydroxyl, cyano, and epoxy moieties, and phenyl substituted with one or more sulfonic acid, sulfonic acid ester, phosphoric acid, phosphoric acid ester, carboxylic acid, carboxylic acid ester, halo, amino, nitro, hydroxyl, cyano, and epoxy moieties.

10. The method of claim 1, wherein R is selected from the group consisting of alkylaryl, arylalkyl, aryl, heteroaryl, $C_1$ to $C_{12}$ primary, secondary or tertiary alkyl groups mono- or polysubstituted by F, Cl, Br, I or CN, phenyl, substituted phenyl groups, cyclohexyl, naphthalenyl, hydroxyl, alkyl ether, perfluoroaryl, sulfonic acid, esters of sulfonic acid, $SF_5$, and F.

11. The method of claim 1, wherein R is selected from the group consisting of phenyl, $C_1$ to $C_{12}$ primary, secondary or tertiary alkyl groups and perfluoroalkyl groups.

12. The method of claim 1, wherein the transition metal catalyst comprises palladium.

13. The method of claim 12, wherein the transition metal catalyst is palladium dichloride-bis-triphenylphosphine.

* * * * *

UNITED STATES PATENT AND TRADEMARK OFFICE
CERTIFICATE OF CORRECTION

PATENT NO. : 8,148,548 B2  
APPLICATION NO. : 12/353609  
DATED : April 3, 2012  
INVENTOR(S) : Steffen Zahn et al.

Page 1 of 2

It is certified that error appears in the above-identified patent and that said Letters Patent is hereby corrected as shown below:

ON THE TITLE PAGE:

Item (56) Col. 2, Line 1 (Other Publication)  
Delete "I5 and I6" and insert -- 15 and 16 -- therefor.

Item (56) Col. 2, Line 21 (Other Publication)  
Delete "Vilsmeir" and insert -- Vilsmeier -- therefor.

IN THE SPECIFICATIONS:

Column 1, Line 15-16  
Delete "POL YMERS" and insert -- POLYMERS -- therefor.

IN THE CLAIMS:

Column 32, Line 43  
In Claim 2, delete "groups," and insert -- groups -- therefor.

Column 32, Line 46  
In Claim 22, delete ""and sulfonic" and insert -- sulfonic -- therefor Column 33, Line 1  
In Claim 5, delete "S ," and insert -- S, -- therefor.

Column 33, Line 5  
In Claim 5, delete "alklthio," and insert -- alkylthio, -- therefor.

Claim 33, Line 20 (Approx.)  
In Claim 5, delete "CH$_2$groups" and insert -- CH$_2$ groups -- therefor.

Signed and Sealed this  
Twenty-second Day of May, 2012

David J. Kappos  
*Director of the United States Patent and Trademark Office*

CERTIFICATE OF CORRECTION (continued)
U.S. Pat. No. 8,148,548 B2

Column 34, Line 65
In Claim 9, delete "claim 1," and insert -- claim 8, -- therefor.

Claim 35, Line 14
In Claim 10, delete "claim 1," and insert -- claim 8, -- therefor.

Claim 36, Line 6
In Claim 11, delete "claim 1," and insert -- claim 8, -- therefor.

Claim 36, Line 9
In Claim 12, delete "claim 1," and insert -- claim 8, -- therefor.

UNITED STATES PATENT AND TRADEMARK OFFICE
CERTIFICATE OF CORRECTION

PATENT NO. : 8,148,548 B2  
APPLICATION NO. : 12/353609  
DATED : April 3, 2012  
INVENTOR(S) : Steffen Zahn et al.

Page 1 of 2

It is certified that error appears in the above-identified patent and that said Letters Patent is hereby corrected as shown below:

ON THE TITLE PAGE:

Item (56) Col. 2, Line 1 (Other Publication)
Delete "I5 and I6" and insert -- 15 and 16 -- therefor.

Item (56) Col. 2, Line 21 (Other Publication)
Delete "Vilsmeir" and insert -- Vilsmeier -- therefor.

IN THE SPECIFICATIONS:

Column 1, Line 15-16
Delete "POL YMERS" and insert -- POLYMERS -- therefor.

IN THE CLAIMS:

Column 32, Line 43
In Claim 2, delete "groups," and insert -- groups -- therefor.

Column 32, Line 46
In Claim 22, delete ""and sulfonic" and insert -- sulfonic -- therefor.

Column 33, Line 1
In Claim 5, delete "S ," and insert -- S, -- therefor.

Column 33, Line 5
In Claim 5, delete "alklthio," and insert -- alkylthio, -- therefor.

This certificate supersedes the Certificate of Correction issued May 22, 2012.

Signed and Sealed this  
Nineteenth Day of June, 2012

David J. Kappos  
*Director of the United States Patent and Trademark Office*

CERTIFICATE OF CORRECTION (continued)
U.S. Pat. No. 8,148,548 B2

Column 33, Line 20 (Approx.)
In Claim 5, delete "$CH_2$groups" and insert -- $CH_2$ groups -- therefor.

Column 34, Line 65
In Claim 9, delete "claim 1," and insert -- claim 8, -- therefor.

Column 35, Line 14
In Claim 10, delete "claim 1," and insert -- claim 8, -- therefor.

Column 36, Line 6
In Claim 11, delete "claim 1," and insert -- claim 8, -- therefor.

Column 36, Line 9
In Claim 12, delete "claim 1," and insert -- claim 8, -- therefor.